United States Patent
Stradella

(10) Patent No.: US 6,938,798 B2
(45) Date of Patent: Sep. 6, 2005

(54) FLUID OR POWDERY PRODUCT DISPENSING DEVICE

(75) Inventor: Giuseppe Stradella, Camogli (IT)

(73) Assignee: TEBRO S.A., Luxembourg (LU)

( * ) Notice: Subject to any disclaimer, the term of this patent is extended or adjusted under 35 U.S.C. 154(b) by 30 days.

(21) Appl. No.: 10/416,873

(22) PCT Filed: Dec. 4, 2001

(86) PCT No.: PCT/EP01/15408
§ 371 (c)(1),
(2), (4) Date: May 15, 2003

(87) PCT Pub. No.: WO02/45866
PCT Pub. Date: Jun. 13, 2002

(65) Prior Publication Data
US 2004/0050885 A1 Mar. 18, 2004

(30) Foreign Application Priority Data
Dec. 8, 2000 (FR) .............................. 00 15998

(51) Int. Cl.⁷ ................................................ B67D 5/00
(52) U.S. Cl. ........................ 222/82; 222/83; 222/209; 222/633
(58) Field of Search ...................... 222/81, 82, 83, 222/209, 386, 632, 633

(56) References Cited

U.S. PATENT DOCUMENTS 3,917,063 A * 11/1975 Chibret et al. .............. 206/221
4,017,007 A    4/1977 Riccio
5,368,201 A * 11/1994 Fuchs ........................ 222/162
5,409,141 A * 4/1995 Kikuchi et al. ............... 222/81
5,511,698 A * 4/1996 Solignac ..................... 222/162
5,568,884 A   10/1996 Bruna
5,893,484 A * 4/1999 Fuchs et al. .................. 222/83
2002/0117513 A1 * 8/2002 Helmlinger .................. 222/82

FOREIGN PATENT DOCUMENTS

| DE | 195 02 725 A | 8/1996 |
| WO | WO 82095626 A | 4/1992 |
| WO | 99/46055 | * 9/1999 .................. 222/82 |

* cited by examiner

Primary Examiner—Joseph A. Kaufman
(74) Attorney, Agent, or Firm—Sughrue Mion, PLLC

(57) ABSTRACT

A device for dispensing a substance in fluid or powder form, the device having a dispensing outlet (10), an air blaster (20) for generating a blast of air when the device is actuated, and at least one reservoir (30) containing a single dose of substance. The reservoir (30) an air inlet (31) connected to the air blaster (20), and a substance outlet (32) connected to the dispensing orifice (10), the air inlet (31) being provided with a substance retaining member (40) for retaining the substance in the reservoir (30) until it is dispensed, and the substance outlet (32) being closed off by a closure element (50). The dispenser device is configured such that the closure element (50) is a spherical element, such as a ball, force fitted into the substance outlet (32) of the reservoir (30). The device further has a mechanical opening system (60, 70, 80) co-operating with the closure element (50) for ejecting it mechanically from its closure position when the device is actuated.

20 Claims, 4 Drawing Sheets

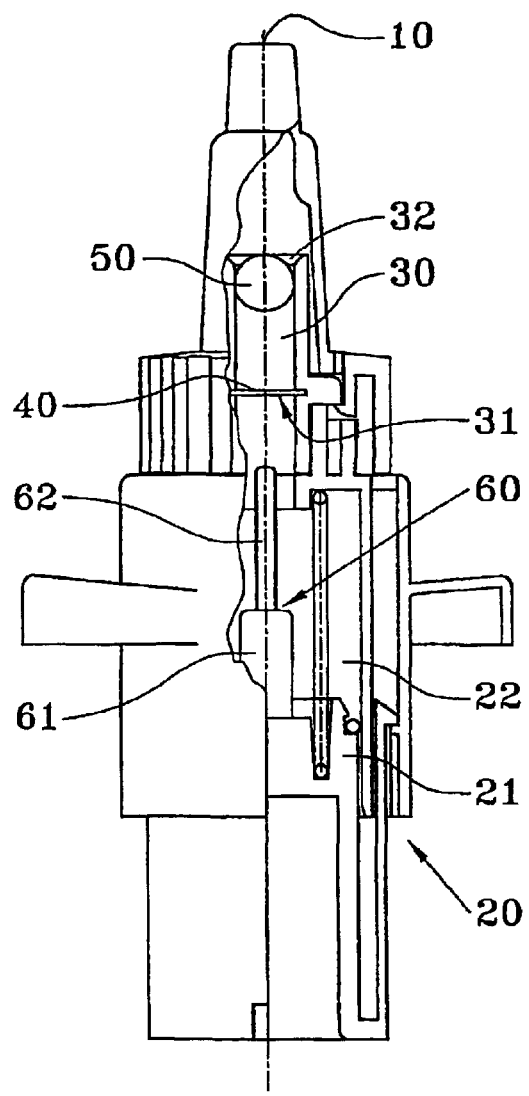
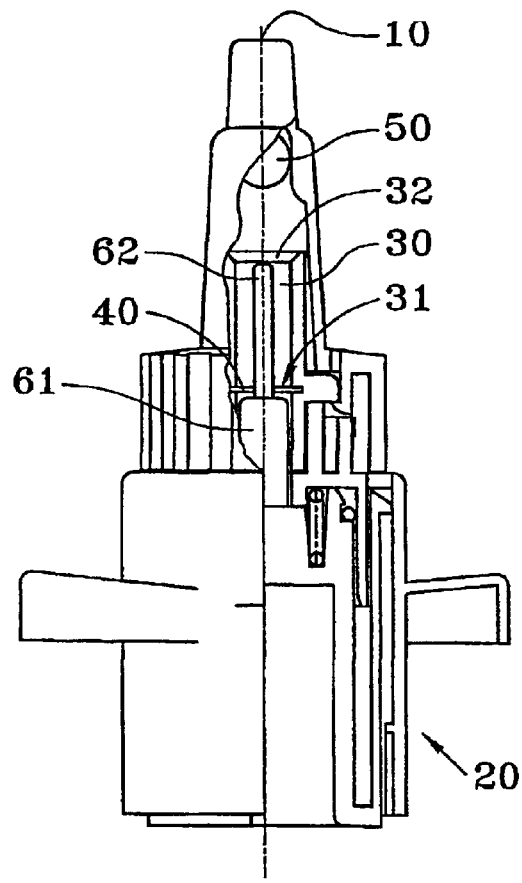
FIG.1
FIG.2

FLUID OR POWDERY PRODUCT DISPENSING DEVICE

FIELD OF THE INVENTION

The present invention relates to a device for dispensing a substance in fluid or powder form, and more particularly to a device for using a flow of air under pressure to dispense a single dose of a fluid or a powder contained in a reservoir.

BACKGROUND OF THE INVENTION

Document WO 99/46055 discloses such a device in which a spherical closure element that closes off the outlet of the reservoir is ejected by the blast of air generated by an air blaster. More particularly for using a powder dispenser device, the air pressure necessary to actuate the device must be high enough to guarantee that the dose is dispensed in full, and that it is broken up if necessary. In the above-mentioned device, the air pressure required to actuate the device is determined by the resistance of the ball to being ejected. That resistance is relatively difficult to control and to predetermine since it depends on the friction between the ball and its cylindrical seat in which it is fitted to close off said reservoir in leaktight manner. Therefore, it can be necessary to minimize the interference between the sphere and its cylindrical seat, which naturally can degrade the effectiveness of closure. In addition, it can be necessary to minimize the depth and the positioning of the sphere in its seat in order to facilitate ejecting it. It can also be necessary to provide air pressure that is relatively high and that is not always easy to achieve by means of a pump system or of a bellows system, in particular when such air blasters are actuated manually by the patient. In addition, the dispensing, i.e. the ejection of the ball from its seat, can take place at various lengths of the stroke of the pump or of the bellows of the air blaster, so that the precise instant at which the fluid or powder is dispensed cannot always be predetermined exactly. Finally, the choice of materials for the sphere and for its seat is limited.

OBJECTS OF THE INVENTION

An object of the present invention is to provide a device for dispensing a substance in fluid or powder form that does not reproduce the above-mentioned drawbacks.

An object of the present invention is thus to provide a fluid or powder dispenser device in which the ejection of the closure element that closes off the reservoir in leaktight manner is independent of the air pressure delivered by the air blaster.

Another object of the present invention is to provide a fluid or powder dispenser device of the above-mentioned type that is simple and inexpensive to manufacture and to assemble.

Yet another object of the present invention is to provide such a fluid or powder dispenser device that makes it possible to use an air blaster that is simple and inexpensive, and that does not require a particularly powerful blast of air to be generated.

A further object of the invention is to provide such a fluid or powder dispenser device that guarantees that the dose of fluid or powder is dispensed in full, and that it is broken up, if necessary.

To these ends, the present invention provides a device for dispensing a substance in fluid or powder form, the device comprising a dispensing outlet, an air blaster for generating a blast of air when the device is actuated, and at least one reservoir containing a single dose of the substance, said reservoir having an air inlet connected to said air blaster, and a substance outlet connected to said dispensing orifice, said air inlet being provided with a substance retaining member for retaining the substance in the reservoir until it is dispensed, and said substance outlet being closed off by a closure element, said dispenser device being characterized in that the closure element is a spherical element, such as a ball, force fitted into the substance outlet of the reservoir, said device further comprising a mechanical opening system co-operating with said closure element for ejecting it mechanically from its closure position when the device is actuated.

Preferably, the closure element is a spherical element, such as a ball, force fitted into the substance outlet of the reservoir.

In a first variant, said substance retaining member is impermeable to the substance and impermeable to air, before the device is actuated.

In a second variant, said substance retaining member is impermeable to the substance and permeable to air before the device is actuated.

In a first embodiment of the invention, said substance retaining member is a membrane which is punctured by said mechanical opening system when the device is actuated.

Advantageously, said mechanical opening system comprises a movably mounted rod adapted to pass through said reservoir when said device is actuated so as to eject said closure element.

Advantageously, said rod comprises a first rod portion secured to said air blaster and a second rod portion fixed to said first rod portion, and designed to puncture said membrane and to pass through said reservoir so as to expel said closure element.

Advantageously, said first rod portion is provided with at least one external air-passageway groove extending axially or helically along said rod.

In a second embodiment of the invention, said mechanical opening system is secured to said substance retaining member.

Advantageously, the substance retaining member is a plate which is extended inside the reservoir towards the closure element by a preferably conical first rod whose end co-operates with the closure element.

Advantageously, said air blaster further comprises a second rod which co-operates with said retaining member to move it together with the first rod when the device is actuated.

Advantageously, said second rod is provided with at least one external air passageway groove.

Advantageously, the substance retaining member is provided with one or more air passageway grooves.

In a third embodiment of the invention, the reservoir comprises a powder reservoir and a liquid reservoir, and the substance retaining member comprises a first retaining member which, at rest, separates the two reservoirs, and a second retaining member, the mechanical opening system comprising a rod interconnecting said two retaining members so that, when the rod moves, the liquid is firstly transferred into the powder reservoir to mix with the powder therein, the closure element being ejected mechanically at the end of the stroke of the rod by said first retaining member, air passageway means being opened to connect the air blaster to the powder reservoir so as to deliver the powder and liquid mixture through said substance outlet.

Preferably, said mechanical opening system forms a guide system for manually actuating the air blaster.

In a first embodiment, said air blaster comprises a piston mounted to slide in an air chamber.

In a second embodiment, said air blaster comprises a bellows.

BRIEF DESCRIPTION OF THE DRAWINGS

Other characteristics and advantages of the present invention will appear more clearly on reading the following detailed description of embodiments of it, with reference to the accompanying drawings, which are given by way of non-limiting example, and in which:

FIG. 1 is a diagrammatic section view of a first embodiment of a fluid or powder dispenser device of the invention, in the rest position;

FIG. 2 is a view similar to the FIG. 1 view, in the actuating position;

DETAILED DESCRIPTION OF THE INVENTION

Figure 3:
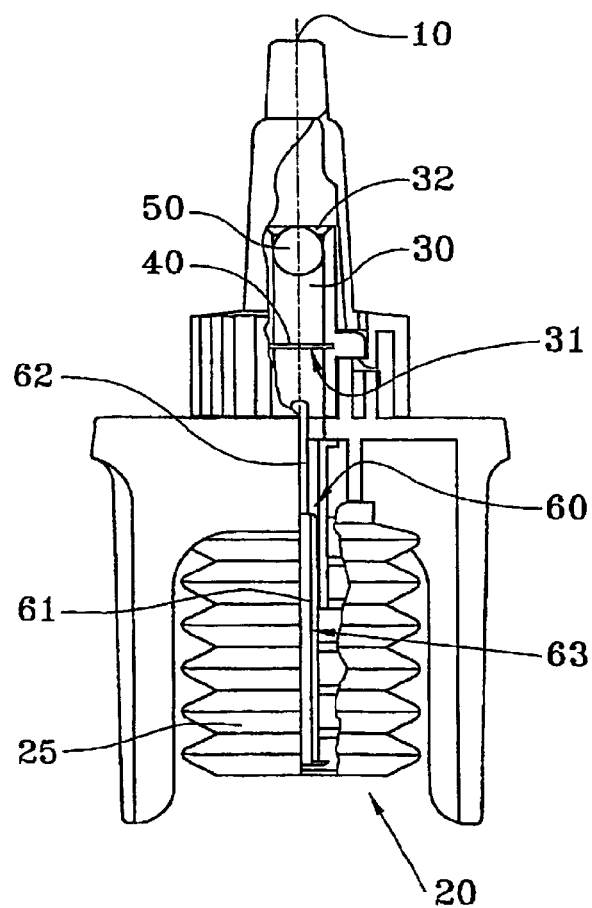
FIG. 3 is a diagrammatic section view showing a variant of the first embodiment of FIGS. 1 and 2, in the rest position.

The present invention, in its variants and embodiments described below, relates more particularly to a device of the type disclosed in Document WO 99/46055. That document is thus incorporated herein by way of reference as regards general operation of the device, and more particularly the spherical closure element disposed at the outlet of the reservoir. Therefore, only those elements which constitute the present invention are described in detail below.

However, it is understood that the present invention is not limited to that type of device, but rather it is applicable to all types of fluid and powder dispenser devices that have reservoirs closed off by spherical closure elements, a requirement being that the contents of the reservoir must be delivered by a blast of air.

FIGS. 1 and 2 show a first embodiment of the present invention. The device comprises a reservoir 30 provided with an air inlet 31 and with a fluid or powder outlet 32. The air inlet 31 of the reservoir is connected to an air blaster 20, and the fluid or powder outlet 32 of the reservoir is connected to a dispensing outlet 10 of the device. The fluid or powder outlet 32 is closed off by a spherical closure element 50, such as a ball, which is force fitted into said fluid or powder outlet 32. The air inlet 31 is provided with a fluid or powder retaining member 40 which is adapted to retain the fluid or powder in the reservoir before the device is actuated. The air blaster 20 is actuated manually by the user and is adapted to generate a blast of air which passes through the reservoir 30 to convey the fluid or powder contained therein towards the dispensing outlet 10.

In the invention, the device further comprises a mechanical opening system 60 which is preferably secured to the air blaster 20, i.e. it is actuated simultaneously with actuation of said air blaster 20, which is adapted to co-operate with said closure element 50 so as to eject it mechanically from its closure position when the device is actuated. In the example shown in FIGS. 1 and 2, the mechanical opening system 60 comprises a rod assembly 61, 62 made up of a first rod portion 61 which is secured to the air blaster 20, and of a second rod portion 62 which is preferably of smaller diameter, which is fixed to said first rod portion 61, and which is adapted to pass through, and in particular to puncture, the fluid or powder retaining member 40, and then to pass through the reservoir 30 until it co-operates with the closure element 50 for the purpose of ejecting it mechanically from its closure position.

The fluid or powder retaining member 40 may advantageously be implemented in the form of a membrane which is impermeable to the fluid or powder, but which is permeable to air. In this way, at the beginning of actuation of the air blaster 20, the pressure increases both in the air blaster and in the reservoir 30, so that, when the ball 50 is ejected by the second rod portion 62, the fluid or powder contained in the reservoir 30 is sprayed finely towards the dispensing outlet 10 of the device. Naturally, the fluid or powder retaining member 40 may also be implemented so as to be impermeable both to the fluid or powder and also to air, prior to actuation of the device, the air pressure generated by the air blaster penetrating into the reservoir 30 only when said membrane 40 is punctured.

Advantageously, the first rod portion 61 is provided with at least one external air-passageway groove 63 adapted to transmit the blast of air when the ball 50 is ejected. Said groove(s) may be straight, i.e. axial, or else they may be helical, so as to provide the breaking-up that can be required in order to achieve fine spraying, in particular when the substance to be dispensed is a powder.

The air blaster shown in FIGS. 1 and 2 comprises a piston 21 mounted to slide in an air chamber 22, the piston 21 being actuated manually by the user. The presence of the rod, and in particular of the first rod portion 61, guides said piston 21, thereby facilitating actuation of said piston, by constraining it to move axially, inside the chamber 22.

Figure 4:
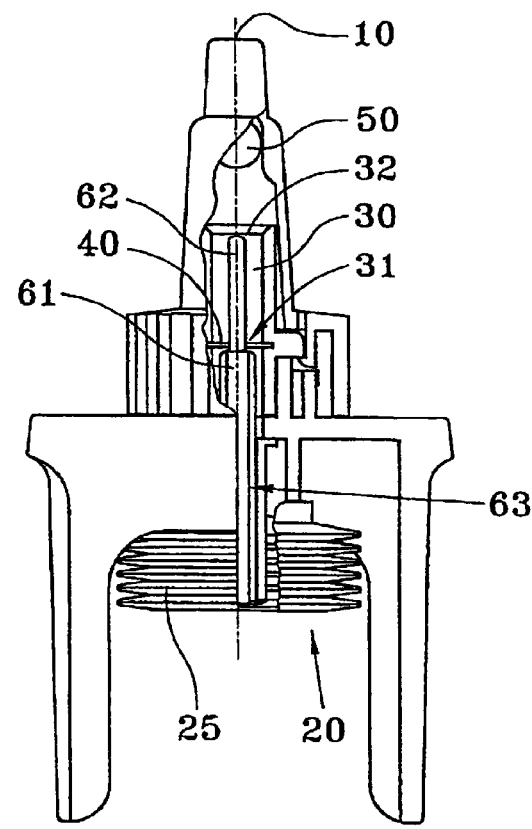
FIG. 4 is a view similar to the FIG. 3 view, in the actuating position.

FIGS. 3 and 4 show a variant embodiment of the device shown in FIGS. 1 and 2, in which the air blaster is implemented in the form of a bellows 25. In this variant too, the first rod portion 61 provides guiding for actuation of said bellows 25, thereby enabling the bellows 25 to be implemented very simply, without having to provide complicated guide means, since guiding is already obtained by said rod 61 disposed centrally inside said bellows.

Figure 5:
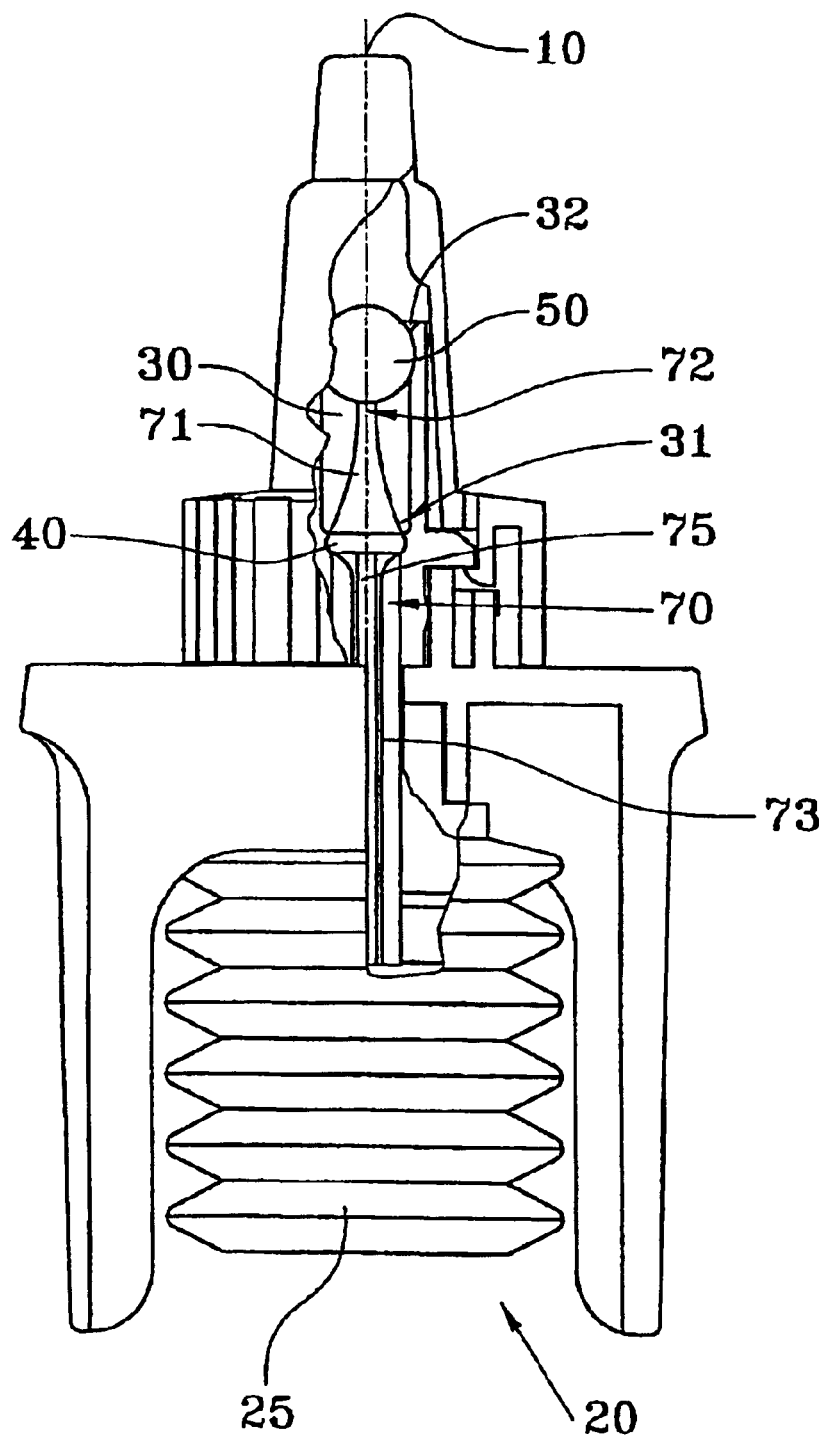
FIG. 5 is a diagrammatic section view of a second embodiment of a fluid or powder dispenser device of the present invention, in the rest position.

FIG. 5 shows a second embodiment of the present invention. Unlike what occurs in the first embodiment (described above), in the second embodiment, the fluid or powder retaining member 40 is not designed to be punctured by the mechanical opening system 70, but rather it forms part of said system. Thus, said fluid or powder retaining member 40 is advantageously implemented in the form of a rigid disk which is extended inside the reservoir by a first rod 71 whose end 72 co-operates with the closure element 50. The first rod 71 is preferably implemented conically, or with a similar shape, which makes it possible firstly to provide sufficient space for the fluid or powder contained in the reservoir, and secondly to guarantee good diffusion of the blast of air generated by the air blaster 20 on delivering the fluid or powder. On its other side, the fluid or powder retaining member 40 is extended by a second rod 75 which is secured to the air blaster 20. The second rod 75 is adapted to move the retaining member 40, and therefore the first rod 71, and thus the closure element 50 when the air blaster 20 is actuated. Advantageously, the movement of the second rod 75 takes place at the end of the actuation stroke of the air blaster, in order to deliver a flow of air under pressure when the ball 50 is ejected.

Advantageously, the second rod 75 is also provided with one or more external air passageway grooves for transmitting the blast of air to the inside of the reservoir 30 when the device is actuated. The fluid or powder retaining member 40 may be either completely impermeable to air in its rest position, so that the blast of air penetrates into the reservoir 30 only when the ball 50 is ejected, or else it may be provided with one or more air passageway grooves which make it possible for the pressure of the air to increase also inside the reservoir 30 at the beginning of actuation of the air blaster 20, and until said ball 50 is ejected. Such an increase in pressure in the reservoir prior to delivery of the fluid or powder substance can also facilitate breaking up the substance, in particular when the substance is powder.

In the example shown in FIG. 5, the air blaster 20 is a bellows 25, advantageously guided by the second rod 75, as explained above, but clearly any type of air blaster can be used, and in particular the piston system shown in FIGS. 1 and 2.

The present invention thus provides a fluid or powder dispenser device in which it is possible to increase the interference between the ball and the fluid or powder outlet 32 of the reservoir 30, which results in closure that is more reliable, in particular in terms of leaktightness. In addition, because the interaction can be greater, and because the ball is no longer ejected by the blast of air, the most suitable materials can be chosen to make said ball and said seat provided at the fluid or powder outlet 32 of the reservoir 30. In addition, it is easy to adjust the pressure when the fluid or powder is dispensed, merely by modifying the length of the rod 61, 75 which co-operates with the air blaster 20. The longer the rod, the sooner the ball 50 is ejected in the actuation stroke of the air blaster, and the weaker the flow of air when the fluid or powder is dispensed.

Figures 6, 7, 8:
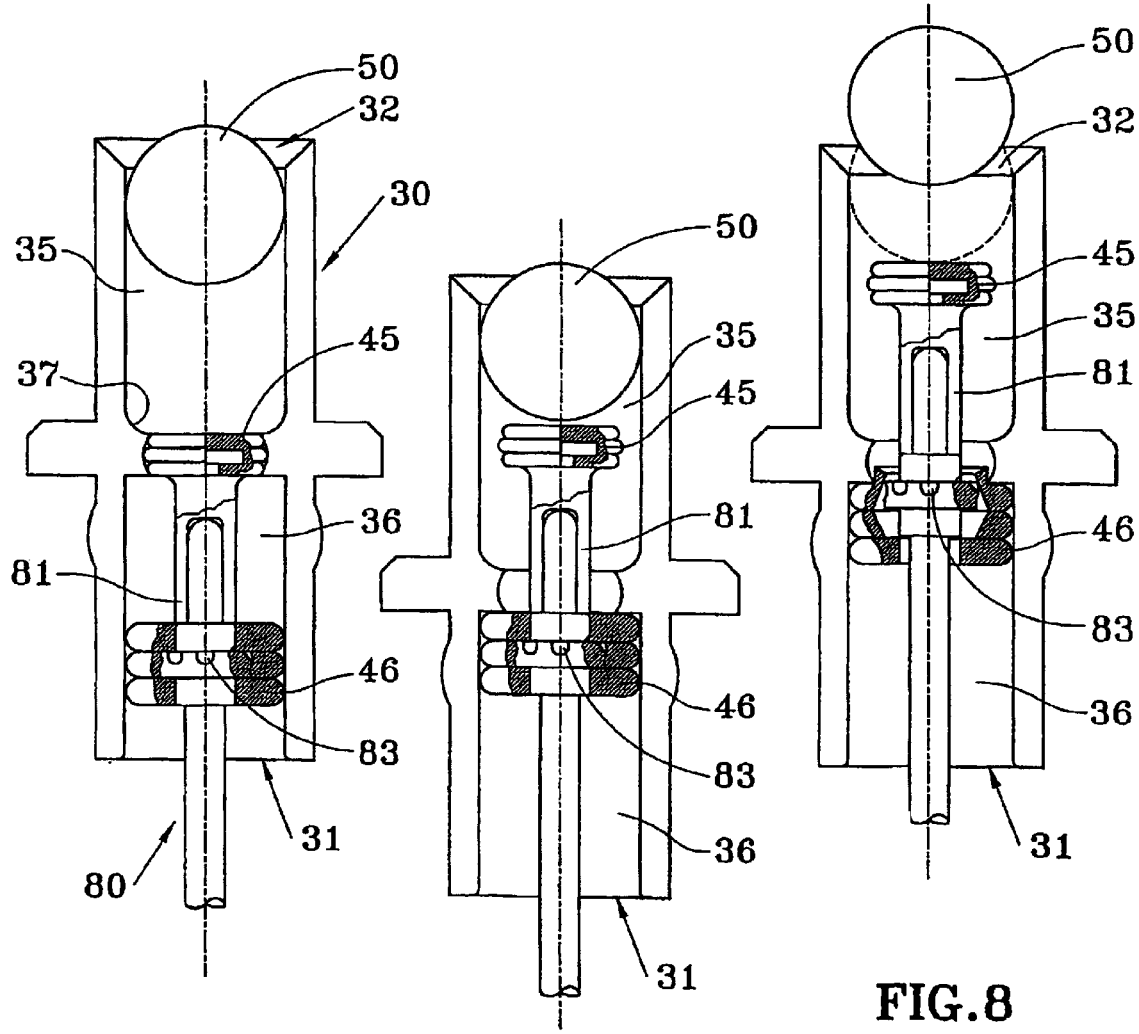
FIGS. 6, 7, and 8 are diagrammatic section views of a third embodiment of the invention, respectively in the rest position, in the post-mixing position, and in the dispensing position.

Although described mainly with reference to a powder, the present invention also applies to dispensing liquids. In particular, as shown in FIGS. 6 to 8, it is possible to imagine applying it to a device comprising a reservoir 30 formed of reservoir of powder 35 and of a reservoir of liquid 36, the powder and the liquid being to be mixed before they are dispensed. For this purpose, the reservoir 30 is separated by a separator wall 37 which is provided with an opening that is closed off at rest by a first retaining member 45 which separates the powder reservoir 35 from the liquid reservoir 36, preferably in leaktight manner. A second retaining member 46 is provided in the liquid reservoir 36. In the example shown in figures, the top reservoir is the powder reservoir 35 and the bottom reservoir is the liquid reservoir, but this configuration could be inverted. The mechanical opening system 80 comprises a rod 81 which is preferably secured to the air blaster (not shown). This rod firstly drives the two retaining members 45 and 46 so that the opening between the two reservoirs is opened up, and the liquid is then transferred into the powder reservoir 35 by the action of the second retaining member which forms a piston in the liquid reservoir 36. In the position shown in FIG. 7, all of the liquid has been transferred into the powder reservoir 35, in which the two materials mix. The second retaining member 46 then forms the retaining member for the powder and liquid mixture. The first retaining member 45 is disposed very close to the closure element 50. Since the rod 81 is secured to the air blaster, the movement between FIGS. 6 and 7 creates air compression. The rod 81 continuing to exert thrust from the position shown in FIG. 7 firstly deforms the second retaining member 46 so that the air passageway openings 83 provided in the rod 81 are opened so as to connect the air blaster to the reservoir 35. Secondly, the closure element 50 is ejected mechanically by the first retaining member 45, pushed by the rod 81. Thus, the powder and liquid mixture is delivered from the reservoir 35 through the outlet 32 of the reservoir 30 by means of the compressed blast of air generated by the air blaster.

The invention is also applicable to a multi-dose device having a plurality of individual reservoirs, means then being provided for causing a respective reservoir to co-operate with the air blaster and with the mechanical opening system each time the device is actuated.

The present invention is described with reference to several variants, but naturally a person skilled in the art can make any modifications thereto, without going beyond the ambit of the present invention as defined by the accompanying claims.

What is claimed is:

1. A device for dispensing a substance in fluid or powder form, the device comprising a dispensing orifice (10), an air blaster (20) for generating a blast of air when the device is actuated, and at least one reservoir (30) containing a single dose of substance, said reservoir (30) having an air inlet (31) connected to said air blaster (20), and a substance outlet (32) connected to said dispensing orifice (10), said air inlet (31) being provided with a substance retaining member (40) for retaining the substance in the reservoir (30) until it is dispensed, and said substance outlet (32) being closed off by a closure element (50), said dispenser device being characterized in that the closure element (50) is a spherical element force fitted into the substance outlet (32) of the reservoir (30), said device further comprising a mechanical opening system (60, 70, 80) having a rigid member engaging said closure element (50) for ejecting it mechanically from its closure position when the device is actuated.

2. A device for dispensing a substance in fluid or powder form, the device comprising a dispensing orifice, an air blaster for generating a blast of air when the device is actuated, and at least one reservoir containing a single dose of substance, said reservoir having an air inlet connected to said air blaster, and a substance outlet connected to said dispensing orifice, said air inlet being provided with a substance retaining member for retaining the substance in the reservoir until it is dispensed, and said substance outlet being closed off by a closure element, wherein the closure element is a spherical element force fitted into the substance outlet of the reservoir, said device further comprising a mechanical opening system co-operating with said closure element for ejecting said closure element mechanically from its closure position when the device is actuated; and in which said mechanical opening system (60, 70, 80) is secured to said air blaster (20).

3. A device according to claim 1, in which said substance retaining member (40) is impermeable to the substance and is impermeable to air, before the device is actuated.

4. A device according to claim 1, in which said substance retaining member (40) is impermeable to the substance and permeable to air before the device is actuated.

5. A device according to claim 1, in which said substance retaining member (40) is a membrane which is punctured by said mechanical opening system (60) when the device is actuated.

6. A device according to claim 5, in which said mechanical opening system (60) comprises a movably mounted rod (61, 62) adapted to pass through said reservoir (30) when said device is actuated so as to eject said closure element (50).

7. A device according to claim 6, in which said rod comprises a first rod portion (61) secured to said air blaster (20) and a second rod portion (62) fixed to said first rod portion (61), and designed to puncture said membrane (40) and to pass through said reservoir (30) so as to expel said closure element (50).

8. A device according to claim 7, in which said first rod portion (61) is provided with at least one external air-passageway groove (63) extending axially or helically along said rod.

9. A device according to claim 1, in which said mechanical opening system (70) is secured to said substance retaining member (40).

10. A device according to claim 9, in which the substance retaining member (40) is a plate which is extended inside the reservoir (30) towards the closure element (50) by a preferably conical first rod (71) whose end (72) co-operates with the closure element (50).

11. A device according to claim 10, in which said air blaster (20) further comprises a second rod (75) which co-operates with said retaining member (40) to move it together with the first rod (71) when the device is actuated.

12. A device according to claim 11, in which said second rod (75) is provided with at least one external air passageway groove (73).

13. A device according to claim 9, in which the substance retaining member (40) is provided with one or more air passageway grooves.

14. A device according to claim 1, in which the reservoir (30) comprises a powder reservoir (35) and a liquid reservoir (36), and the substance retaining member (40) comprises a first retaining member (45) which, at rest, separates the two reservoirs (35, 36), and a second retaining member (46), the mechanical opening system (80) comprising a rod (81) interconnecting said two retaining members (45, 46) so that, when the rod (81) moves, the liquid is firstly transferred into the powder reservoir (35) to mix with the powder therein, the closure element (50) being ejected mechanically at the end of the stroke (81) of the rod by said first retaining member (45), air passageway means (83) being opened to connect the air blaster to the powder reservoir (35) so as to deliver the powder and liquid mixture through said substance outlet (32).

15. A device according to claim 1, in which said mechanical opening system (60, 70, 80) forms a guide system for manually actuating the air blaster (20).

16. A device according to claim 1, in which said air blaster (20) comprises a piston (21) mounted to slide in an air chamber (22).

17. A device according to claim 1, in which said air blaster comprises a bellows (25).

18. The device according to claim 1, wherein the closure element is a ball.

19. A device for dispensing a substance in fluid or powder form, comprising:
a dispensing outlet;
an air blaster having a compressible chamber that generates a blast of air when the device is actuated;
a reservoir containing a dose of a substance, the reservoir having an air inlet communicating with the air blaster and a substance outlet communicating with the dispensing orifice, the air inlet provided with a seal that retains the substance in the reservoir until the substance is dispensed, and the substance outlet closed off by a closure element, wherein the closure element fitted into the substance outlet of the reservoir, and wherein the device further comprises a movable rigid member co-operating with the closure element so as to contact and mechanically eject the closure element from closure element's closing position when the device is actuated.

20. The device according to claim 19, wherein the mechanical opening system is secured to the air blaster.

* * * * *